United States Patent
Simmons et al.

(10) Patent No.: US 6,521,683 B1
(45) Date of Patent: Feb. 18, 2003

(54) ANTISTATIC AGENTS AND RESIN COMPOSITIONS INCORPORATED THEREIN

(75) Inventors: Roy Simmons, Collierville, TN (US); William P. Chatham, Memphis, TN (US); Michael L. Whitlock, Atoka, TN (US); James J. Ward, Tecumseh, MO (US)

(73) Assignee: Witco Corporation, Greenwich, CT (US)

( * ) Notice: Subject to any disclaimer, the term of this patent is extended or adjusted under 35 U.S.C. 154(b) by 0 days.

(21) Appl. No.: 09/298,870

(22) Filed: Apr. 26, 1999

(51) Int. Cl.⁷ .................... C08K 5/3445; C08K 5/375; C08L 33/12; C07D 233/04; D06M 13/352; C08J 3/20

(52) U.S. Cl. .................... 524/158; 524/236; 524/560; 524/910; 252/8.91; 548/347.1

(58) Field of Search ................. 524/236, 158, 524/560, 910; 252/8.84, 8.86, 8.91; 548/347.1, 350.1, 354.1; 510/327, 328, 329, 330

(56) References Cited

U.S. PATENT DOCUMENTS

| | | | |
|---|---|---|---|
| 3,277,079 A | * 10/1966 | Press | 536/31 |
| 3,985,939 A | 10/1976 | Kleber et al. | |
| 4,255,294 A | * 3/1981 | Rudy et al. | 510/331 |
| 4,623,589 A | 11/1986 | Simmonds, Jr. | |
| 4,696,950 A | 9/1987 | Cox | |
| 4,781,983 A | 11/1988 | Stickley | |
| 4,888,119 A | * 12/1989 | Klewsaat | 8/137 |
| 4,891,143 A | * 1/1990 | Woodward et al. | 510/321 |
| 4,904,825 A | 2/1990 | Govindan | |
| 4,973,616 A | 11/1990 | Govindan | |
| 5,011,937 A | 4/1991 | Govindan | |
| 5,053,531 A | 10/1991 | Govindan | |
| 5,187,214 A | 2/1993 | Govindan | |
| 5,254,269 A | * 10/1993 | Taylor et al. | 510/328 |
| 5,491,187 A | 2/1996 | Ward, et al. | |
| 5,658,651 A | * 8/1997 | Smith et al. | 442/59 |
| 5,804,313 A | * 9/1998 | Schell | 428/391 |
| 5,858,960 A | * 1/1999 | Conroy et al. | 510/521 |
| 6,120,757 A | * 9/2000 | Dubrief et al. | 424/70.9 |

FOREIGN PATENT DOCUMENTS

GB 1189477 * 4/1970

OTHER PUBLICATIONS

Ward, James, Simmons, Roy, and Chatham, Philip; "Internal Anti–Static Agents for Engineering Plastics", Annual Technical Conference, Society of Plastics Engineers, 56(2), 1998 (pp. 1782–1786).*

* cited by examiner

Primary Examiner—Vasu Jagannathan
Assistant Examiner—Callie E. Shosho
(74) Attorney, Agent, or Firm—Hoffmann & Baron, LLP

(57) ABSTRACT

Antistatic agents for reducing and eliminating static electric charges on resins, particularly acrylic resins, including an antistatically effective amount of at least one substituted imidazolinium salt of alkylbenzene sulfonic acid having the formula:

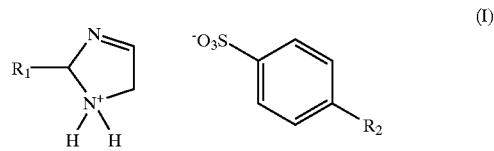

(I)

wherein $R_1$ and $R_2$ are the same or different and are alkyl groups having 6 or more carbon atoms. Also contemplated are methods, compositions and articles of manufacture which include the above mentioned antistatic agent and are added to or on the resins and further contain fatty acids or optical brighteners.

32 Claims, No Drawings

ANTISTATIC AGENTS AND RESIN COMPOSITIONS INCORPORATED THEREIN

FIELD OF INVENTION

The present invention relates to compositions and methods for reducing and eliminating static electric charges on resins, particularly acrylic resins, by adding to or on the resins an antistatic agent that includes an antistatically effective amount of at least one substituted imidazolinium salt of alkylbenzene sulfonic acid. Antistatic articles of manufacture are also contemplated.

BACKGROUND OF TECHNOLOGY

Synthetic polymers have many commercial uses. They can be readily formed and machined to provide a variety of shapes. Their desirable qualities include crystal clarity, good surface hardness, relatively good resistance to scratches, good chemical resistance and excellent weatherability. Synthetic polymers and in particular acrylic polymers, have many applications such as electrical insulators, automotive instrument panel covers, automotive tail lights, paneling, safety glazing, medical application, sanitary and laboratory wear, aircraft canopies and domes, signage, and the like.

Many polymers are essentially electric insulators, that is, they are non-conductors of electricity. A conductor of electricity has the ability to transmit a stream of electrons and thus carry an electrical current. On the other hand, insulators may become negatively or positively charged and cannot easily dissipate the charge. Therefore, articles prepared from such polymers tend to develop static electric charges upon their surfaces when they are subjected to friction during their production and finishing or during their handling or use. Static electric charges on surfaces are undesirable because they readily attract dust and other contaminants, which may interfere with the smooth finish of the article, making it unsightly and difficult to clean. This will cause the article to be cleaned more frequently and increase the tendency for the surface to be scratched. Additionally, static electric charges may accumulate to a level where sparks may occur when the static charge discharges. This spark can act as an ignition source for flammable materials and vapors, creating severe safety hazards. Also, an unpleasant electric shock may be experienced when the article is handled and the electric charge discharges. Additionally, static electric charges may also cause problems in the processing of resins.

To eliminate the undesirable static electric charges on resins, antistatic agents have been added to polymers and other non-conductive materials. Antistatic agents facilitate the transfer of electrons to eliminate static electric charges on the surface of a material and can be added externally or internally. External antistatic agents may also be applied to the surface of a finished product. Such coatings while useful, may be less desirable if they are easily removed when contact is made with the surface. Application of external antistatic agents is generally performed by spraying the surface or dipping the article in an antistatic bath.

Internal antistatic agents, i.e., agents which are added to resin composition often self-migrate or bloom to the surface of the polymer, thereby effectively reducing or eliminating the accumulation of static electric charges on the surface. As the antistatic agent is wiped away from the surface, more of the agent will migrate to the surface, depending on the type of polymer and chemical structure of the antistatic agent. Such agents are often compounded with the polymer before curing the polymer or forming the finished product.

Acrylic polymers, such as poly(methylmethacrylate), are known to readily accumulate a static electric charge. Efforts to reduce surface charge on these polymers have included chemical treatment of the surface to modify the ester functionality, or incorporating antistatic agents into the resin composition. For example, U.S. Pat. No. 4,973,616 and 5,011,937 issued to Govindan discloses p-toulene sulfonate salts of 2-alkyl imidazolines, e.g., 2-undecyl-4, 4, 5, 5-tetramethyl imidazolinium p-toulene sulfonate. These compounds are said to be useful as internal or external antistatic agents for fibers, such as acrylic fibers and synthetic polymers, such as polystyrene. Additionally, U.S. Pat. No. 5,491,187 issued to Ward et al. discloses methods for reducing or eliminating static electric charges on resins by adding to the resins an effective amount of at least one substituted ammonium salt of a alkylbenzene sulfonic acid having the general formula:

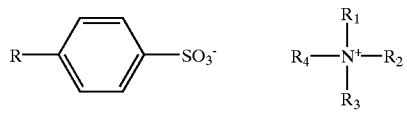

wherein R is straight or branched chain alkyl group having 10 to 14 carbon atoms, $R_1$ is hydroxyethyl or an alkyl group having 1 to 6 carbon atoms, $R_2$ and $R_3$ are the same or different and are hydroxyethyl, an alkyl group having from 1 to 6 carbon atoms or hydrogen, and $R_4$ is hydrogen or an alkyl group having from 1 to 6 carbon atoms. Resins incorporating these agents tend to yellow due to the lack of thermal stability of the agent.

Antistatic compositions desirably possess several important properties including a short decay time, that is, a short time to dissipate a static electric charge. Antistatic agents are desirably compatible with the resin to which they are added so that they will not change the color properties of the resin at processing temperatures. For example, a clear polymer resin may become yellow or opaque if an incompatible antistatic agent is used. Additionally, it is desired that the antistatic agent be thermogravimetrically stable during processing. Many of the prior art antistatic agents and compositions fail to posses one or more of these properties. Accordingly, there is a need for antistatic agents and compositions which possess these attributes.

SUMMARY OF THE INVENTION

One aspect of this invention contemplates an antistatic agent including at least one substituted imidazolinium salt of alkyl benzene sulfonic acid, said salt having the formula:

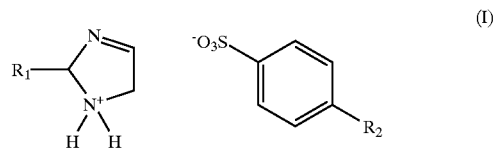

(I)

wherein $R_1$ and $R_2$ are the same or different and are alkyl groups having 6 or more carbon atoms.

Another aspect of the invention there is included an antistatic resin composition including:

a) a synthetic or natural resin; and b) at least one substituted imidazolinium salt of alkyl benzene sulfonic acid; said salt having the formula:

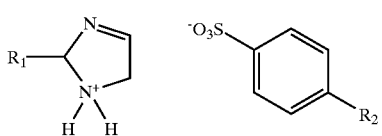

(I)

wherein $R_1$, and $R_2$ are the same or different and are alkyl groups having 6 or more carbon atoms. Various other additives such as fatty acids and optical brighteners may also be added to the resin composition.

A further aspect of this invention provides a method for treating an article to reduce accumulation of static electric charge thereon, including the steps of selecting an article to be treated and applying to said article an antistatically effective amount of a composition including at least one substituted imidazolinium salt of alkylbenzene sulfonic acid, said salt having formula (I) wherein $R_1$ and $R_2$ are the same or different and are alkyl groups having 6 or more carbon atoms.

Another aspect of this invention includes a method for making an antistatic compositions selecting a resin composition which accumulates static electric charge on its cured surface; and incorporating in said resin composition, prior to curing, an antistatically effective amount of a composition comprising at least one substituted imidazolinium salt of alkyl benzene sulfonic acid said salt having the above-mentioned formula (I) wherein $R_1$ and $R_2$ are the same or different and are alkyl groups having 6 or more carbon atoms.

A further aspect of this invention provides an article of manufacture including a cured synthetic or natural resin; having at least one substituted imidazolinium salt of alkylbenzene sulfonic acid; said salt having the formula:

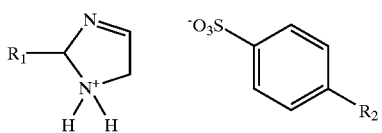

(I)

wherein $R_1$ and $R_2$ are the same or different and are alkyl groups having 6 or more carbon atoms incorporated therein.

Also included in this invention is an article of manufacture coated with the aforementioned antistatic agent. The antistatic agents of the present invention conforming to the aforementioned formula are also believed to represent novel salts. Thus, another aspect of this invention relates to an antistatic agent including a salt of an alkaryl sulfonic acid and an organic base including hydrophilic groups thereon, the agent being capable of reducing static electric charges when applied to or incorporated in a resin.

DETAILED DESCRIPTION OF THE INVENTION

The antistatic agents of the present invention have been found to be of particular use to create antistatic compositions in combination with resins which have a tendency to build-up static electric charge. These antistatic agents are substituted imidazolinium salts of alkylbenzene sulfonic acids, conforming to the following formula:

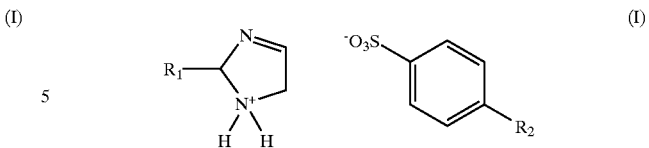

(I)

wherein $R_1$ and $R_2$ are the same or different and are an alkyl group having 6 or more carbon atoms. The alkyl groups may be linear, branched and aliphatic groups. The salts are generally a gel-like material at room temperature and in use may be diluted with a fluid carrier. Carriers which are useful include solvents such as petroleum based oils. Mineral oil, kerosine, and other similar oils may be used. Desirably, the fluid carrier or solvent has little or no offensive odor.

The novel antistatic agents are added to resin compositions in amounts sufficient to decrease the resins static charge decay time. Generally, the antistatic agent is added to resin compositions in amounts of about 0.5% to about 2% by weight of the resin composition. More desirably, however, the antistatic agent is present in the resin composition in amounts of about 0.75% to about 1.5% by weight of the resin composition. However, the upper limit of the antistatic agent present is largely dictated by cost factors as well as potential adverse affects on the properties of the resin. The lower limits of antistatic agents present in the resin is dictated by the ability to decrease static electric charge.

Antistatic resin compositions of the present invention can include synthetic and natural resins, as well as combinations of these resins. Numerous synthetic resins may be employed. Non-limiting examples include acrylic resins, polyolefins, styrene resins, polyesters, ethylene glycol-terephthalic acid polymers, polyamides, polyacetals, vinyl resins, poly(phenylene ether) resins and combinations thereof. Particular resins that may be used include poly(methylmethacrylate), polypropylene, polystyrene, poly(styrene-acrylonitrile-butadiene)terpolymers, poly(vinylacetate), polyethylene, ethylene glycol terephthalic acid polymers, polycarbonates, polyamides, poly(vinylbutyral), phenol-formaldehyde, poly(vinyl chloride), poly(vinylidene chloride), poly(-phenylene ether) and combinations thereof Acrylic resins such as poly(methylmethacrylate) are particularly useful because of their tendency to build-up static electric charge in the absence of the antistatic agent.

Examples of natural resins and natural-combinations include rayon, acetate, rayon-cellulose materials such as cellulose acetate-propionate, cellulose butyrate, cotton, linen, jute, ramie, wool, mohair, glass, fiberglass, and alike. Various textile constructions and individual fibers of these materials may be used in combination with the antistatic agents of the present invention.

Antistatic resin compositions may also include a variety of conventional additives which serve to promote the effectiveness of the antistatic agent. For example, various long chain fatty acids and optical brighteners may be added to the compositions. These additives may be incorporated as a pre-mix with the antistatic agent and carrier, or added directly to the resin composition.

As mentioned above, the novel antistatic agents may be used as a coating to a resin composition or incorporated into the composition per se. When incorporated into the resin composition, the agents tend to migrate due to their ionic structure and geometry and can bloom to the surface of the resin. Consequently, as antistatic agent is wiped off the surface of a resin, additional antistatic agent may bloom to the resin surface.

Typically fatty acids having from 6 to 24 carbon atoms have been found to be useful. In certain preferred embodiments of the invention, saturated fatty acids may be employed. Lauric acid, myristic acid, palmitic acid, stearic acid, arachidic acid, palmitoleic acid, oleic acid, ricinoleic acid, linoleic acid, arachidonic acid, behenic acid and combinations of these acids are particularly desirable. The upper limit of the fatty acid additive is generally dependent upon the specific salt employed and its properties and the lower quantity of fatty acid is generally the level at which handling of the salt is improved. For example, the fatty acid may be employed in about 50 to about 150 weight percent of the salt. For example, a premix of the salt in fatty acid can be employed with such amounts. In certain embodiments, equal amounts of the salt in fatty acid may be found to be useful.

Among the specific antistatic salts found to be particularly useful as antistatic agents and for incorporation for use with resin compositions are imidazolinium dodecylbenzene sulfonate and 2-undecylimidazolinium dodecylbenzene sulfonate. Combinations of these salts and others from formula (I) above are contemplated. In general, the salts of the present invention are formed from the reaction of alkaryl sulfonic acids and organic bases which desirably include hydrophilic groups.

Resin compositions such as those containing acrylic polymers are usually prepared with a free radical catalyst. Preparation of these polymers can be by various processes including bulk processing, suspension polymerization, emulsion or solution polymerization. The polymers are typically available in various physical forms including sheets, rods, tubes, pellets and beads. The antistatic agents of the present invention can readily be added to the polymer by conventional means. For example, extrusion, injection molding, compression molding or casting may be employed. While the antistatic agents may be applied to plastic surfaces, longevity of antistatic properties are enhanced when the antistatic agents are added as internal agents to the polymers.

The antistatic agent may be blended with the resin by conventional methods such as by mixing or extrusion. The resins may be added as a premix or directly to the resin composition. Moreover, a master batch technique can be employed. For example, a concentrated mixture of the antistatic agent and the polymer may be extruded into pellet forms. These pellets can then be mixed with additional polymer to produce the appropriate concentration. The antistatic agents of the present invention have good thermostability so they can be used in the typical processing temperatures of the chosen polymer.

The antistatic behavior of the articles and compositions of this invention is tested using static decay tests (Federal Test Standards 101C Method 4046). In this test, the resin plaque is charged to 5,000 volts DC. The test is carried out for both the positive charge and a negative charge. After charging, the plaque is grounded and the time required for 90% discharge is measured. The test is somewhat dependent upon humidity, so the testing is done in a humidity-controlled chamber. Therefore, the humidity can be controlled at whatever level is desired. Normally, antistatic agents are more effective at high humidities. As the antistatic effect improves, the discharge time decreases. Thus, a lower time is indicative of greater antistatic effect. Polymers which contain no antistatic agent often will not even accept the initial 5,000-volt charge.

The following examples are given to illustrate embodiments of the invention and it is understood that these examples are illustrative and the invention is not to be considered as restricted thereto.

EXAMPLE 1

This example describes a method of producing an antistatic agent of this invention. In a two liter beaker, 326 grams of Witco 1298 soft acid (dodecylbenzene sulfonic acid) are mixed using a magnetic stirrer with 1200 milliliters of isopropyl alcohol (IPA). To this, was slowly added 256.4 grams of 2-undecylimidazoline, as a coarse powder, until the solution changes from green to yellow. This color change is an indication that the solution has been neutralized. A commercial grade pH meter was used to determine the pH of the solution and further 2-undecylimidazoline was added to neutralize the solution, if necessary. The solution was concentrated using a rotary evaporator to remove the IPA. A melt blend of 1080 grams of Hystrene 9718 (stearic acid 95% pure) was added to the 2-Undecylimidazolinium dodecylbenzene sulfonate salt (UIDBS) and was poured onto a sheet of aluminum foil to allow to solidify upon cooling, and then broken up into small chunks.

EXAMPLE 2

This example demonstrates a method of making an antistatic agent of the present invention. In a one liter beaker, 55.0 grams of Hystrene 9718 (stearic acid 95% pure) was added to 200 ml of isopropyl alcohol. To this, 22.4 grams of ground 2-undecylimidazoline and 32.6 grams Witco 1298 soft acid was added. The mixture was stirred with a magnetic stirrer and heated until all the 2-undecylimidazoline was dissolved. The mixture was transferred to a one liter round bottom flask and the isopropyl alcohol was removed by rotary evaporation. The product was poured onto aluminum foil and allowed to cool. The resulting product was determined to be 2-undecylimidazolinium dodecylbenzene sulfate with a melting point of 64° C.

EXAMPLE 3

This example describes another method for making an antistatic agent of the present invention. In a one liter beaker, 29.8 grams of 1298 Witco soft acid was added to 300 ml of methanol. To this beaker 22.4 grams of ground 2-undecylimidazoline was added. The mixture was stirred with a magnetic stirrer and was heated until the 2-undecylimidazoline was dissolved. The mixture was poured into a one liter round bottom flask and the methanol was removed by rotary evaporation. The product was a thick gel and poured into a 1 quart jar. The resulting product was determined to be imidazolinium dodecylbenzene sulfonate.

EXAMPLE 4

This example describes an antistatic agent of the present invention being incorporated into a resin composition. An appropriate amount of 2-undecylimidazolinium dodecylbenzene sulfonate (UIDBS) of the present invention in gel form was added to poly(methylmethacrylate) pellets (PMMA) and mixed by kneading in a plastic bag so that the pellets were thoroughly coated with a antistatic agent. The resulting mixture was put into a commercial grade heat extruder at a temperature of 240° C. and run through the extruder three times to ensure correct formulation. This same procedure was used with gels of the prior art antistatic agents, as will be shown below in Table 2.

This extrusion process produced an intimate, homogeneous mixture of antistatic agent in the acrylic plastic. The compression molded plaques were about 7 inches on each side and about 0.075 inches thick. A sample which is about 3 inches wide and about 7 inches long was cut from the plaque for testing in the following examples.

EXAMPLE 5

Three 30-gram plaques containing a 1.5% of 2-Undecylimidazolinium dodecylbenzene sulfonate in PMMA were made. Plaques containing imidazolinium dodecylbenzene sulfate in plexiglass were made at 105° C., 210° C. and 185° C. and dried at 210° C. for 30 minutes. It noted that the 210° C. dried plaque looked excellent, but contained bubbles throughout the plaque.

EXAMPLE 6

A plaque containing 2% by weight of the PMMA resin composition of 2-Undecylimidazolinium dodecylbenzene sulfonate in plexiglass acrylic resin was dried for 3 hours at 105° C. The resulting plaque did not contain any bubbles and had static decay times as displayed in Table 1.

EXAMPLE 7

A study comparing currently available commercial antistatic agents in poly(methylmethacrylate) (PMMA) with the antistatic agents in PMMA of the present invention is set forth in Table 2 and Table 3. The maximum percent of antistatic agent employed in these tests was approximately 2.0% by weight of the resin composition, that is, the concentration of antistatic agent incorporated into the PMMA had a maximum of about 2.0% by weight.

Thermogravimetric analysis (TGA) was performed using a Mettler TG50 to measure the stability of the PMMA with the antistatic agent. The temperature was raised from 30° C. to 250° C. at a rate of 20° C. per minute under a nitrogen blanket and then held under nitrogen for an additional 5 minutes at 250° C. The results listed in the tables are reported as percent weight loss.

Static decay times were measured to determine the effectiveness of the antistatic agent in reducing the static electric charge. This was done by measuring 10 mil compression molded plaques using an Electro-Tech Systems Faraday Cage with Federal Test Standards 101C Method 4046 as the test method. In this test, the plaque is charged to 5,000 volts DC. The test is carried out for both a positive charge and a negative charge. After charging, the plaque is grounded and the time required for 90% discharge is measured. The testing was done in a humidity controlled chamber. The relative humidity was kept approximately constant at either approximately 15% or 70% so that comparisons could be made.

Optical measurements were also performed on the plaques to determine the polymer compatibility with the antistatic agent and the tendency for the antistatic agent to form a color or become opaque in the resin at processing temperatures. The optical measurements were made on the compression molded plaques using a HunterLab ColorQUEST spectrophotometer to measure the yellowness index. The yellowness index measures the color change caused by the antistatic agent, with the lower number indicating less color change in the PMMA.

The TGA, static decay and optical measurements for each of the samples tested are given in Table 2. A TGA weight loss of less than 5% and a static decay time of less than 0.5 seconds were deemed desirable. Low color indices were also desirable. Plaques incorporating known antistatic agents, dioctyl sodium sulfosuccinate, disodium sulfosuccinate, glycerol monolaurate, sodium xylene sulfonate, lauramide diethanolamide and tetrabutylphosphonium dodecylbenzene sulfonate failed to charge during the static decay test, indicating that they are comparatively not effective as an internal antistatic agent for PMMA under our test conditions. Additionally, as evidenced from Table 2, the known antistatic agent sodium dodecylbenzene sulfonate, although effective as an internal antistatic agent for PMMA, rendered the plaques opaque and undesirable for use.

Antistatic agents in PMMA tested and used in accordance with the invention are shown in Table 3. It was concluded from these tests that a soft organic base containing hydrophilic groups in combination with an alkaryl sulfonic acid would yield an effective antistatic agent. Ethanolamine, triethanolamnine and undecylimidazoline were used in combination with linear and branch alkaryl sulfonic acids. The results are presented in Table 3. The patented salt of undecylimidazoline with toluene sulfonic acid is shown for comparison.

As shown in table 3, prior art antistatic agents, ethanolammonium linear dodecylbenzene sulfonate, ethanolammonium branched dodecylbenzene sulfonate, ethanolammonium tridecylbenzene sulfonate, and triethanolammonium linear dodecylbenzene sulfonate imparted unacceptable color to the resin. The prior art antistatic agent 2-undecylimidazolinium toluenesulfonate demonstrated low yellowing, but comparatively slow static decay as compared to the inventive 2-undecylimidazolinium dodecylbenzene sulfonate salt of the present invention.

TABLE 1

STATIC DECAY TIMES FOR NOVEL IMIDAZOLINIUM DODECYLBENZENE SULFONATE ANTISTATIC SALTS IN PMMA

| | | | Decay Rate for | |
|---|---|---|---|---|
| | % load | % R.H. | (+) charge | (−) charge |
| Sample 1 | 2% | 48% | 0.13 | 0.14 |
| Sample 2 | 2% | 48% | 0.13 | 0.14 |
| Sample 3 | 2% | 48% | 0.13 | 0.14 |

TABLE 2

TGA, STATIC DECAY AND OPTIC MEASUREMENTS (WHERE NECESSARY) FOR PRIOR ART COMMERCIAL PRODUCTS IN PMMA.

| Antistatic Agent | TGA % Weight Loss | Static Decay sec. (% load, R.H.) | Optical Properties |
|---|---|---|---|
| Disodium Sulfosuccinate | | Would not charge (2, 70) | |
| Diglycerol Monolaurate | | >100 | |
| Glycerol Monolaurate | | Would not charge (2, 70) | |
| Sodium Xylenesulfonate | 45 | Would not charge (2, 70) | |
| Lauramide Diethanolamide | | Would not charge (2, 70) | |
| Ethoxylated Nonylphenol Ether Phosphate Sodium Salt | 14 | 0.58 (0.5, 70) | |
| Dioctyl Sodium Sulfosuccinate | 50 | Would not charge (2, 70) | |
| Quarternary Ammonium Salt | 14 | 0.54 (1.5, 70) | |
| Isopropylammonium Dodecylbenzene Sulfonate | 11 (at 300° C.) | 4 (1.5, 90) | |
| Amido Cocobetaine | 55 | | |
| TEA-Dodecylbenzene Sulfonate | | 0.3 (1.5, 70) | |
| Sodium Dodecylbenzene Sulfonate | 4 (at 300° C.) | 0.12 (1.5, 70) | Opaque |

TABLE 2-continued

TGA, STATIC DECAY AND OPTIC MEASUREMENTS (WHERE NECESSARY) FOR PRIOR ART COMMERCIAL PRODUCTS IN PMMA.

| Antistatic Agent | TGA % Weight Loss | Static Decay sec. (% load, R.H.) | Optical Properties |
|---|---|---|---|
| Tetrabutrylphosphonium Dodecylbenzene Sulfonate | | Would not charge (1.0, 70) | |

TABLE 3

INVENTIVE VS. PRIOR ART ANTISTATIC AGENTS

| Antistatic Agent | TGA % Weight Loss | Static Decay sec. (% load, R.H.) | Optical Properties |
|---|---|---|---|
| PRIOR ART | | | |
| Ethanolammonium Linear Dodecylbenzene Sulfonate | >5 | 0.02 (1, 80) | 9.8 Y.I. |
| Ethanolammonium Branched Dodecylbenzene Sulfonate | >5 | 0.2 (1.5, 70) | visually comparable to 4th entry |
| Ethanolammonium Tridecylbenzene Sulfonate | >5 | 1.2 (1, 70) | visually comparable to 1st entry |
| Triethanolammonium Linear Dodecylbenzene Sulfonate | >5 | 0.3 (1.5, 70) | 13.1 Y.I. |
| 2-Undecyl-imidazolinium Toluenesulfonate | >5 | 1.47 (0.75, 70) | 3.0 Y.I. |
| INVENTIVE | | | |
| 2-Undecyl-imidazolinium Dodecylbenzene Sulfonate | >5 | 0.47 (0.75, 70) | 5.0 Y.I. |

What is claimed:

1. An antistatic agent comprising at least one substituted imidazolinium salt of alkylbenzene sulfonic acid, said salt having the formula:

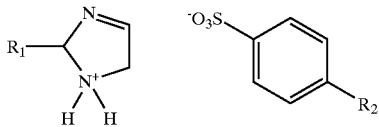

wherein $R_1$ and $R_2$ are the same or different and are alkyl groups having 6 or more carbon atoms.

2. The agent according to claim 1, wherein said salt is diluted with a fluid carrier.

3. The agent according to claim 1, wherein said salt is combined with a petroleum oil carrier.

4. The agent according to claim 1 wherein said salt is combined with a petroleum oil carrier selected from the group consisting of mineral oil, kerosine and combinations thereof.

5. The agent according to claim 1 wherein a fatty acid is admixed therewith.

6. The agent according to claim 1 wherein an optical brightener is admixed therewith.

7. The agent according to claim 1, wherein said salt is imidazolinium dodecylbenzene sulfonate.

8. The agent according to claim 1, wherein said salt is 2-undecylimidazolinium dodecylbenzene sulfonate.

9. The agent according to claim 1 wherein said alkyl group is a linear, branched, or acrylic aliphatic group.

10. An antistatic resin composition comprising:
   a) a synthetic or natural resin; and
   b) at least one substituted imidazolinium salt of alkylbenzene sulfonic acid; said salt having the formula:

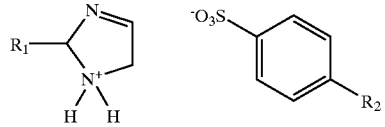

wherein $R_1$ and $R_2$ are the same or different and are alkyl groups having 6 or more carbon atoms.

11. The composition according to claim 10 wherein the imidazolinium salt is present in an amount sufficient to decrease the static charge decay time.

12. The composition according to claim 10 wherein said imidazolinium salt is present in amounts of about 0.5% to about 2.0% by weight.

13. The composition according to claim 10 wherein said resin is an acrylic resin.

14. The composition according to claim 10 wherein said resin comprises poly(methylmethacrylate).

15. The composition of claim 10, wherein said resin is selected from the group consisting of rayon, acetate, rayon-cellulosic resins, wool, mohair, ramie, glass, fiberglass, fiberglass insulation, cellulose butyrate, cotton, linen, jute and combinations thereof.

16. The composition according to claim 10 wherein said resins is selected from the group consisting of acrylic, polyolefins, styrene, polyesters, ethylene glycol-terephthalic acid polymers, polyamides, polyacetals, vinyls, poly (phenylene ether), and combinations thereof.

17. The composition according to claim 10 wherein the resin is selected from the group consisting of poly(methylmethacrylate), polypropylene, polystyrene, poly(styrene-acrylonitrile-butadiene)terpolymers, poly(methylacrylate), poly(vinylacetate), polyethylene, ethylene glycol terephthalic acid polymers, polycarbonates, polyamides, poly(vinylbutyral), phenol-formaldehyde, poly(vinyl chloride), poly(vinylidene chloride), poly(-phenylene ether) and combinations thereof.

18. The composition according to claim 10 further including a material selected from the group consisting of fatty acids and optical brighteners.

19. The composition according to claim 18 wherein said fatty acid is selected from the group consisting of lauric, myristic, palmitic, stearic, arachidic, palmitoleic, oleic, ricinoleic, linoleic, arachidonic acids and combinations thereof.

20. The composition according to claim 10 wherein $R_1$ and $R_2$ are $C_6$–$C_{24}$ alkyl.

21. The composition according to claim 10 wherein said salt is imidazolinium dodecylbenzene sulfate.

22. The composition according to claim 10 wherein said salt is 2-undecylimidazolinium dodecylbenzene sulfonate.

23. The composition of claim 10 wherein said alkylbenzene sulfonic acid is dodecylbenzene sulfonic acid.

24. A method of treating an article to reduce accumulation of static electric charge thereon comprising:
   a) selecting said article to be treated; and b) applying to said article an antistatically effective amount of a composition comprising at least one substituted imidazolinium salt of alkylbenzene sulfonic acid, said salt having the formula:

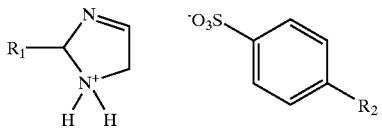

wherein $R_1$ and $R_2$ are the same or different straight alkyl group having 6 or more carbon atoms.

25. The method of claim 24 wherein $R_1$ and $R_2$ are $C_6$–$C_{24}$ alkyl.

26. The method of claim 24 wherein said antistatic composition is applied to said article after said article is in a finished state.

27. The method of claim 24 wherein said antistatic composition is applied to said article before said article is in a finished state.

28. A method of making an antistatic composition comprising:

a) selecting a resin composition which accumulates static electric charge on its cured surface; and b) incorporating in said resin composition, prior to curing, an antistatically effective amount of a composition comprising at least one substituted imidazolinium salt of alkyl benzene sulfonic acid said salt having the formula:

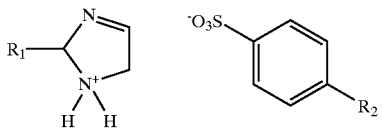

wherein $R_1$ and $R_2$ are the same or different and are alkyl groups having 6 or more carbon atoms.

29. An article of manufacture comprising:

a) a cured synthetic or natural resin having at least one substituted imidazolinium salt of alkyl benzene sulfonic acid; said salt having the formula:

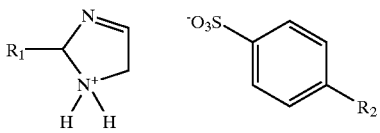

wherein $R_1$ and $R_2$ are the same or different and are alkyl groups having 6 or more carbon atoms incorporated therein.

30. A compound having the formula:

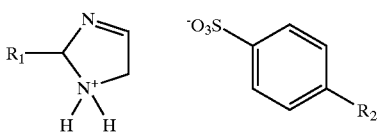

wherein $R_1$ and $R_2$ are the same or different and are alkyl groups having $C_6$–$C_{24}$.

31. The compound according to claim 30 wherein the compound is 2-undecylimidazolinium dodecylbenzene sulfonate.

32. An antistatic agent comprising the salt of:

a) an alkaryl sulfonic acid; said alkyl group having $C_6$–$C_{24}$; and b) an organic base comprising imidazoline base including hydrophilic groups thereon; said agent effectively reducing static electric charges when applied to or incorporated on a resin.

* * * * *